United States Patent [19]

Ying

[11] Patent Number: 5,688,502
[45] Date of Patent: *Nov. 18, 1997

[54] ANIMAL GROWTH PROMOTANT

[75] Inventor: Thomas Ko Sai Ying, Victoria, Australia

[73] Assignee: Enzacor Properties Limited, St. Helier, Channel Islands

[*] Notice: The term of this patent shall not extend beyond the expiration date of Pat. Nos. 5,356,625 and 5,567,423.

[21] Appl. No.: 694,092

[22] Filed: Aug. 8, 1996

Related U.S. Application Data

[63] Continuation of Ser. No. 230,007, Apr. 19, 1994, Pat. No. 5,567,423, which is a continuation of Ser. No. 833,587, Feb. 12, 1992, abandoned, which is a continuation of Ser. No. 328,075, filed as PCT/AU87/00269, Aug. 17, 1987, abandoned.

[30] Foreign Application Priority Data

Aug. 28, 1986 [AU] Australia .................... PH 7714/86

[51] Int. Cl.$^6$ .................................................. A61K 38/54
[52] U.S. Cl. .................. 424/94.3; 424/94.61; 424/94.63; 424/94.65
[58] Field of Search ................... 424/94.3, 94.61, 424/94.63, 94.65

[56] References Cited

U.S. PATENT DOCUMENTS

| | | | |
|---|---|---|---|
| 5,356,625 | 10/1994 | Ying | 424/94.1 |
| 5,567,423 | 10/1996 | Ying | 424/94.3 |

*Primary Examiner*—Bruce R. Campell
*Attorney, Agent, or Firm*—Iver P. Cooper

[57] ABSTRACT

A growth promotant comprising microgranules having a core consisting of one or more enzymes selected from: i) protein digesting enzymes; ii) carbohydrate digesting enzymes; iii) fat digesting enzymes; and iv) fiber digesting enzymes in an immobilized form; the core being encapsulated within a water soluble film, and coated with an enteric coating comprising an alkali soluble, acid insoluble polymer, or a high molecular weight polymer whose structure is substituted with or contains windows of fatty acid or other material capable of being solubilized by intestinal juices. A method for increasing animal growth comprising the administration of a growth promoting amount of the growth promotant is also described, as is a method of producing the growth promotant.

26 Claims, No Drawings

ANIMAL GROWTH PROMOTANT

This is a continuation of application Ser. No. 08/230,007 filed Apr. 19, 1994, U.S. Pat. No. 5,567,423, itself a continuation of application Ser. No. 07/833,587, filed Feb. 12, 1992, now abandoned, itself a continuation of application Ser. No. 07/328,075, filed Feb. 23, 1989, now abandoned, which is the national stage of PCT/AU87/00269, filed Aug. 17, 1987, all hereby incorporated by reference.

The present invention relates to in vivo growth promotion in animals, and more specifically pertains to a growth promotant, processes for its production and methods for increasing animal growth.

Growth promotion in animals, particularly domestic animals, has in the past been achieved by the addition of catabolic steroidal substances such as oestrogen to animal feed. Recently, this practice has fallen into disfavour, as unacceptably high amounts of the steroids accumulate in animal tissues. As a result, undesirable effects arise such as the development of breasts in male children who consume chickens fed large amounts of oestrogen.

Another wide-spread practice is the incorporation of antibiotics into animal feed. This helps to control opportunistic bacterial infection, creating overall better health of stock with consequent weight gain. This practice has come under close scrutiny from health authorities, and has been condemned as facilitating the production of antibiotic resistant strains of micro-organisms. This is of particular concern where the antibiotics used as feed additives are commonly prescribed human therapeutics.

It has further been proposed to promote animal growth using various digestive enzymes as feed additives. These enzymes help to break down crude feed material in the intestines, thereby making increased amounts of nutrient materials available for adsorption for a given food ration, over that available under normal digestive conditions.

The incorporation of enzymes into feed has the disadvantage that the enzymes are often denatured and inactivated on passage through the stomach or rumen, where extremes of pH are encountered. As enzymes have specific requirements for pH, temperature, cofactors, etc. for maintenance of their biological activity, deviation from optimal values may lead to reduction in enzyme activity or enzyme inactivation which may be irreversible. It has been found that the addition of digestive enzymes to animal feed has generally been ineffective in promoting animal growth. Furthermore, as only a small proportion of administered enzymes survive passage through the rumen or stomach, large amounts of enzymes are required thereby making such a treatment uneconomical.

Australian Patent No. 516,072 proposes to protect digestive enzymes from gastric inactivation by mixing them with a binding system, a stabiliser, and disintegrant, then coating the mixture with an enteric coating. The enteric coating allows passage through the stomach, whereafter it breaks down in the alkaline environment of the duodenum. The binder and disintegrant facilitate rapid liberation of the enzymes into the duodenum. This proposal has the disadvantage that the digestive enzymes are partially inactivated on blending them with a binding agent and a disintegrant, in the presence of organic solvents such as isopropanol and methylene chloride. Further, the digestive enzymes are also partially inactivated by organic solvent when an enteric coating is applied. The granular size of particles produced according to U.S. Pat. No. 516,072 are generally unsatisfactory, due to their large size which prevents uniform distribution through feed.

A requirement accordingly exists for an enzymic animal growth promotant which overcomes one or more of the abovementioned disadvantages.

The present invention seeks to provide a growth promotant for the effective utilization of feed components.

According to the present invention there is provided a growth promotant comprising microgranules having a core consisting of one or more enzymes selected from:

(i) protein digesting enzymes, (ii) carbohydrate digesting enzymes, (iii) fat digesting enzymes, or (iv) fibre digesting enzymes in an immobilized form, the core being encapsulated with a water soluble film, and coated with an enteric coating comprising an alkali soluble acid insoluble polymer, or a high molecular weight polymer whose structure is substituted with or contains windows of fatty acid or other material capable of being solubilized by intestinal juices.

The term "immobilized form" refers to the enzymes being immobilized within a gel-like material, enclosed within a semi-permeable membrane, adsorbed onto adsorbing agents or bound to chelating agents.

Enzymes may be immobilized, for example, by any of the following methods:

(a) The entrapment method—The incorporation of enzymes into the core of a gel like material or enclosure within a semi-permeable membrane;

(b) The cross-linking method—Intermolecular cross-linking of enzymes utilizing crosslinking reagents; or (c) The carrier binding method—The physical or chemical binding of enzymes to a water insoluble substance by ionic and/or covalent bonds.

The immobilization is carried out so that the enzymes retain their biological activity.

The entrapment of enzymes within a core may be carried out by the admixture of the enzymes with agents capable of forming a gel under certain conditions, such that the enzymes are entrapped within the formed gel matrix.

Examples of gel-forming agents include k-carrageenan, gelatin, alginates, cellulose or its derivatives, or various gel-forming synthetic polymers such as polyamides or chitosan. If an absorbing agent is used it is preferably microfined activated charcoal.

Chelating agents useful in the immobilization of enzymes include EDTA, its salts or derivatives, and high molecular weight hydrophilic polymers such as polyacrylamides or high molecular weight salts capable of disassociating their ionic bond in aqueous solution et aqueous/hydrophilic solvent.

The particle size of the microgranules is preferably between 25 and 500 µm, and more preferably between 50 and 350 µm.

Examples of enzymes which may be used in the present invention include:

(1) Protein digesting enzymes (proteolytic enzymes)

cathepsin a, b and c glandular kallekriens, proteinase K, subtilisin, ficin, streptodornase, papain, rennin, trypsin, bromelin and any protease from bacterial, fungal, plant or animal origin, (2) Carbohydrate digestive enzymes amylase, glucoamylase, maltase, lactase, β-glucanase, glucose isomerase, glucose oxidase, invertase and any carbohydrate digesting enzyme of bacterial, fungal, plant or animal origin, (3) Fat digesting enzymes pancreatic lipase, bacterial and fungal lipase, (4) Fibre digesting enzymes
cellulase, pectinase, hemicellulase.

Encapsulation involves the deposition of a thin film or a mechanical barrier over the core enabling physical separation of the core of each microgranule and its environment. This barrier or film is soluble in aqueous solution. An example of a compound forming a suitable mechanical barrier is gelatin.

The enteric coating is preferably cellulose acetate phthalate. However, any other acid resistant, alkali soluble polymer may be utilized.

Butyl methacrylate or other high molecular weight polymers may be substituted with or contain windows of stearic acid or any other fatty acid derivative, such as $CH_{12-24}$ fatty acids, capable of being solubilized by intestinal juice.

The immobilization of digestive enzymes within a gel is a most advantageous feature. Particularly, the gel matrix restricts the accessibility of denaturing agents, such as organic solvents used in the application of an enteric coating (an acid insoluble, base soluble coating such as cellulose acetate phthalate), to the enzymes. A significant proportion of the digestive enzymes immobilized within the gel matrix are thus ultimately available for catalytic activity. This is to be contrasted with the results achieved in the prior art, where a significant loss of enzyme activity occurs on application of enteric coatings.

The gel matrix in which the digestive enzymes may be immobilized is porous and permeable. Accordingly, when the gel is exposed to aqueous conditions, such as the environment of the duodenum, the gel swells due to the entry of intestinal juice into the gel matrix, and the digestive enzymes are released and pass out of the gel for catalytic activity.

Microgranules of a very small particle size, in the order of 50 μm to 500 μm, may be produced without the loss of biological activity of the digestive enzymes according to the practice of the present invention. Particularly, digestive enzymes immobilized within a gel, or in a solution capable of forming a gel are easy to handle and process, and may be subject to gentle procedures to produce microgranules of the desired small particle size. For example, a gel containing digestive enzymes may be extruded through a sieve of very small pore size, or may be freeze dried to give particles of the desired size. Alternatively, digestive enzymes in a solution capable of forming a gel, may be sprayed, through a suitable nozzle to form fine droplets which pass into a solution which causes the droplets to gel, thereby immobilizing the digestive enzymes within the formed gel matrix. The size of the granule formed in this manner is determined by the pore size in the nozzle and the pressure at which the solution is atomized. In contest, such results cannot be obtained by prior art approaches. In the prior art, enzymes are merely mixed with conventional binding agents which are not susceptible to the above treatments to produce microgranules of the desired particle size.

Microgranules of a small particle size are most desirable, as they may be evenly distributed through feed, and allow rapid release of enzymes, due to the increased surface area of the microgranules.

The provision of a water soluble barrier about the enzyme containing core, provides protection against denaturation of the enzymes by organic solvents used during application of an enteric coating. Because of the protective nature of the gel matrix mentioned earlier, a significant maintenance of biological activity of the digestive enzymes is achieved. This in turn means that considerable economy in the quantities of digestive enzymes utilised for growth promotion can be achieved.

The growth promotant of the present invention Enables pH sensitive digestive enzymes to be protected from inactivation in the stomach or the rumen, yet be available for action in the intestinal tract, particularly the duodenum. When the growth promotant reaches the alkaline regions of the intestine of monogastric animals, the outer coating is dissolved, or the fatty acid windows are digested. Intestinal juice is then able to pass to the water soluble coating causing it to be degraded. This exposes the core, causing it to swell and release digestive enzymes.

In ruminant animals, a high molecular weight polymer such as butylmethacrylate with fatty acid windows, preferably $C_{12-24}$, allows the passage of the growth promotant through the rumen and the stomach. In the intestinal regions, particularly the duodenum, fatty acid windows are digested by lipases, thus allowing the water soluble coating to be degraded and the core exposed, causing it to swell and release digestive enzymes. It is to be noted in this regard, that the small particle size of the microgranules, which may be achieved according to the practice of the present invention, facilitates the passage of microgranules through the rumen.

According to a further aspect of the present invention, there is provided a method for increasing the growth of animals by the administration of an effective amount of a growth promotant as hereinbefore described.

Animals treated according to the above method show increased weight gain and improved feed utilization.

Animals which may be treated by the present method include pigs, sheep, goats, horses, chickens, ducks, and other domestic animals.

The growth promotant of the present invention may be orally administered to animals.

In another aspect of the present invention, there is provided a composition for increasing animal growth, containing the animal growth promotant as previously described in association with a pharmaceutically acceptable, or veterinarily acceptable carrier or excipient. For example, the growth promotant may be administered with water, kaolin, talc, calcium carbonate, lactose, sodium chloride, copper sulphate, zinc sulphate, ferrosulphate, manganese sulphate, potassium iodide, sulphur, potassium chloride, selenium, and/or vitamins such as biotin, choline, chloride, nicotinamide, folic acid, and vitamins A, D3, E, K, B1, B2 B6 and B12.

According to a still further aspect of the invention, there is provided a food composition for promoting growth in animals, comprising the aforementioned growth promotant in association with an appropriate animal feed stock.

Examples of appropriate animal feed stocks include one or more of the following: maize, wheat, middling, soya bean meat, fish meal, grass meal, skim milk, tricalciumphosphate, malt, corn, rice, milo, whey, alfa-alfa meal, etc.

The various amounts (w/w) of enzyme(s) incorporated into the growth promotant is not critical. The optimal amounts of enzymes to be incorporated into the growth promotant may be readily determined without undue experimentation.

Preferably, each kilogram of the growth promotant, according to the practice of the present invention contains the following:

Protease $2 \times 10^3$ to $2 \times 10^7$ Vitapharm protease units
Amylase: $1 \times 10^4$ to $4.3 \times 10^8$ Vitapharm amylase units
Lipase: 0.5 to $5 \times 10^3$ Vitapharm lipase units
Cellulase: $2 \times 10^2$ to $2 \times 10^6$ Vitapharm cellulase units.

More preferably, one kilogram of growth promotant of the present invention contains:

Protease: $2\times10^5$ protease units
Amylase: $4.3\times10^6$ amylase units
Lipase: $5\times10^1$ lipase units
Cellulase: $2\times10^4$ cellulase units.

Each of the above enzymes are food grade, as defined in the Food Chemical Index, Ed. III.

The enzyme units given above are Vitapharm standard units, and are calculated according to the methods set forth in Example 3.

According to a still further aspect of the present invention, there is provided a process for the production of an animal growth promotant comprising the steps of:

(a) immobilizing one or more enzymes selected from the group consisting of:

(i) protein digesting enzymes;
  (ii) fat digesting enzymes;
  (iii) fibre digesting enzymes;
  (iv) carbohydrate digesting enzymes;

within a core, (b) microgranulating the immobilized enzymes, (c) encapsulating the microgranules with a water soluble mechanical barrier, and (d) coating the microgranules of step (c) with either an alkaline soluble acid insoluble polymer, or a high molecular weight polymer whose structure is interrupted by interstices and windows of fatty acid.

Preferably the microgranules are spray coated with the water soluble mechanical barrier of step (c) and the coating of step (d).

Preferably, immobilization within a core refers to the enzymes being immobilized within a gel-like material.

Animal growth promotants of this invention increase animal weight gain and improve feed utilization. Additionally, the animal growth promotant reduces carcase backfat. This gives leaner meat which is commercially desirable.

The invention will now be further described and illustrated with reference to the following non-limiting examples.

EXAMPLE 1

Method of Preparation of the Animal Growth Promotant (a) 2%–5% w/v of k-carrageenan is mixed with purified water at a temperature of 65° C. until dissolution of the carrageenan is achieved. This solution is then cooled to 50° C.

(b) 1% w/v of equal enzymatic activities (equal enzymatic activities is defined as the amount of enzyme capable of digesting the equal weight of its specific substrate) of amylase, cellulase, protease, and lipase are dissolved in isotonic phosphate buffer solution (40% 0.067M $NaH_2PO_4$ + 60% of 0.67M $Na_2HPO_4$) at pH 6 at 50° C. This solution is added to solution (a) and homogenized at 500 rpm for 15 minutes. 2–5 % w/v of ionized calcium in water is then added to the solution and the resulting solution is homogenized for a further hour at 50 rpm and then cooled to 20° C. giving a gel and an aqueous phase.

(c) The resulting gel and aqueous phase are cooled to 5° C., decanted, filtered and freeze dried. The freeze dried material is milled to give a granule size of 25–100 microns. The granules are then washed with a hardening agent such as 2.5% w/w glutaraldehyde or formaldehyde.

Alternatively, the gel phase of step (b) is extruded and sprayed through 50 µm size pores at 3 kP/cm² and dropped 1–5 meters into 2.5% w/w glutaraldehyde or formalin solution resulting in granule formation.

(d) The granules are then filtered and washed with a softening agent such as glycerol. Any film softener may be used.

(e) The resulting granules are filtered, fluidised and heat dried at 40° C.

(f) The granules of the preceding step are spray coated with 1–2% w/v of gelatin in water solution, at 40° C.

(g) An acid resistant, alkali soluble coating is then spray coated on the granules until the final weight is 120% w/w. The coating comprises:

6% w/w cellulose acetate phthalate

30% w/w isopropanol 0.5% w/w castor oil and acetone to 100% w/w (h) As an alternative to step (g) a high molecular weight polymer whose structure is interrupted by interstices or windows of fatty acid, is spray coated onto the granules until the final weight is 105% w/w. The coating comprises:

3% butyl methacrylate 0.15% dibutylphthalate 0.05% stearic acid and ethyl acetate to 100% w/w.

In step (a) k-carrageenan can be substituted with any gel forming agent such as alginic acid, gelatin, or cellulose and its derivatives.

In step (b), calcium can be substituted with any other alkaline metal ions such as: K, $Rb^{2+}$, $Cs^+$ or alkali metal ions such as $Mg^{2+}$, $Sr^{2+}$ or bi- or tri-valent metal ions such as $Al^{3+}$, $Mn^{2+}$, $B^{2+}$, $Co^{2+}$, $Ni^{2+}$, $Zn^{2+}$, $Pb^{2+}$, etc. or $NH_4^+$ ions or aliphatic amines or aromatic diamines such as triethylamines, methelenediamines, ethylamines, hexamethylenendiamines, etc.

EXAMPLE 2

Growth Promotion in Pigs

Pigs in the "grower phase" (22–50 kilogram live weight) and "finisher phase" (50–80 kilograms live weight) were fed various amounts of the growth promotant of the present invention of Example 1. Each kilogram of the growth promotant comprises $2\times10^5$ protease units, $4.3\times10^6$ amylase units, $5\times10^1$ lipase units and $2\times10^4$ cellulase units. The growth promotant was added to a standard feed stock of wheat, barley, sweet lupin seed, and meat meal. The feed stock contained 13.4 MJ digestible energy per kilogram, 18.3% crude protein, containing 0.95% lysine, 0.54% methionine and 0.56% threonine along with recommended levels of minerals and vitamins.

The six dietary treatments investigated consisted of adding the growth promotant at the rate of 0–1.0, 2.0, 4.0, 8.0 and 16 kilograms per ton of feed. Each treatment was allocated to growing pigs which were fed to a level of three times maintenance which amounted to 84% and 87% of full appetite during the grower (22–50 kilograms) and finisher (50–80 kilograms) phases respectively.

The results of this experiment is given in Table I.

TABLE I

The Performance of Pigs Fed the Growth Promotant Admixed with a Basic Feed Stock

| Growth Promotant - kg/ton | Nil | 1 | 2 | 4 | 8 | 16 |
|---|---|---|---|---|---|---|
| Lightweight gain - | | | | | | |
| 22–50 kg, g/day | 570 | 578 | 575 | 569 | 588 | 577 |
| 50–80 kg, g/day | 732 | 759 | 812 | 791 | 794 | 800 |
| Feed conversion ratio - | | | | | | |
| 22–50 kg | 2.75 | 2.69 | 2.79 | 2.70 | 2.66 | 2.71 |
| 50–80 kg | 3.10 | 2.99 | 2.72 | 2.84 | 2.83 | 2.81 |
| Backfat, $P_2$ mm | 14.1 | 13.4 | 12.9 | 12.8 | 13.1 | 12.1 |
| Carcase dressing % | 68 | 68 | 68 | 68 | 68 | 68 |

From the results shown in Table I, it is evident that the growth promotant of the present invention improved both growth and feed conversion of the test animals. The live weight gain of pigs in the grower phase is not as marked as those in the finisher phase. In the finisher phase, pigs fed no growth promotant showed a light weight gain of 732 grams per day. Pigs fed with 2 kilograms per tonne of growth promotant showed a live weight gain of 812 grams per day. This highlights the efficacy of the present treatment.

While there is no significant differences in carcase dressing percentages between control animals and those animals fed the growth promotant, there appears to be a reduction in carcase backfat (measured using standard callipers) with Increasing level of growth promotant.

EXAMPLE 3

Determination of Vitapharm Standard Units in Respect of Enzyme Activity

A. Protease Units

One Vitapharm protease unit is defined as the amount of enzyme which will liberate 0.0447 milligrams of non-protein nitrogen in a 30 minute colorimetric Hemoglobin Assay. This assay is carried out at pH 4.7, 40° C. using denatured hemoglobin.

Assay
Reagents
  1. Hemoglobin
  2. Powdered Pumice
  3. Hemoglobin Substrate

Weigh 16.0 gm. of Difco Brand Bacto Hemoglobin (moisture-free-basis) into a liter beaker. Add 3 scoops of-powdered pumice and mix the dry ingredients thoroughly. With continuous agitation, add approximately 400 ml. of distilled water and 1 or 2 drops of Dow-Corning Antifoam. Immerse a pH electrode into-the hemoglobin solution and with continuous agitation adjust the pH to 10.0 with 2N sodium hydroxide. Adjust the volume of the solution to 500 ml. Centrifuge the solution for 15 minutes at 3,000 rpm and save supernatant for substrate.

4. Stock Sodium Acetate Buffer, 2M

Dissolve 164 gm. of anhydrous sodium acetate in approximately 700 ml. of distilled water. Using a standardized pH meter, add glacial acetic acid until the buffer is pH 4.70±0.05. Adjust the volume of the solution to 1 liter with distilled water.

5. Sodium Acetate Buffer, 0.2M

Pipette 50 ml. of stock sodium acetate buffer into a 500 ml. volumetric flask and dilute to volume with distilled water.

6. Trichloroacetic Acid (TCA), 70% in distilled water 7. Sodium Hydroxide, 2N 8. Sodium Hydroxide, 0.5N 9. Folin Reagent Dilute 1 volume of Folin-Ciocalteau Phenol Reagent with 2 volumes of distilled water. Dilute phenol reagent is stable for 1 week.

Procedure

1. Pipette 25 ml. of hemoglobin substrate 25 ml. of 0.2M sodium acetate buffer into a 150 ml beaker. With a standardized pH meter determine the pH of the buffered substrate. If the substrate is not pH 4.70±0.05, the pH of the 0.2M sodium acetate buffer must be adjusted so that 25 ml. of hemoglobin substrate and 25 ml. of 0.2M sodium acetate buffer will give pH 4.70±0.05.

2. Pipette 25 ml. of hemoglobin substrate and 25 ml. of 0.2M sodium acetate buffer into a 125 ml. Erlenmeyer flask. Equilibrate the flask in a 40°±0.1° C. water bath for fifteen minutes.

3. At zero time, rapidly pipette 5 ml. of an appropriate enzyme dilution into the equilibrated substrate. Start a stopwatch at zero time.

4. After exactly thirty minutes, add 5 ml. of TCA solution to each flask. For safety, use a burette or pipetting device. Swirl each flask vigorously.

5. Prepare a blank containing 25 ml. hemoglobin substrate, 25 ml. sodium acetate buffer, 5 ml. distilled water, and 5 ml. TCA solution.

6. Allow the flask to stand at room temperature for thirty minutes, allowing the protein to coagulate completely. Filter each solution through Whatman No. 42 filter paper. It is advisable to refilter the first half of the filtrate through the same filter. The filtrate must be absolutely clear.

7. Pipette 1 ml. of each filtrate, 4 ml. of 0.5N sodium hydroxide, and 1 ml. of dilute phenol reagent into a test tube and mix well.

8. After ten minutes, and not more than twenty minutes, determine the absorbance of each filtrate at 660 nm against the blank.

Calculations

One Hemoglobin Unit (HU) is the amount of enzyme which will liberate 67.08 mg. ($5^{3/2} \times 6 = 67.08$) of non-protein nitrogen under the conditions of the assay.

$$HU/gm = \frac{\Delta A \times F}{W}$$

ΔA = absorbance of enzyme digest filtrate at 660 nm

F = fixed relationship between color development by phenol reagent and protease hydrolysis. See standardization procedure for explanation.

W = mg. of enzyme added to digest in 5 ml. aliquot.

Standard Procedure

Different proteases cleave different peptide bonds. There is no universal relationship between color development by phenol reagent and the extent of hydrolysis. However, a fixed relationship does exist for each type of protease. The fixed relationship, i.e. F factor, can be determined by incubating hemoglobin substrate with a sample of known hemoglobin activity. The incubation is followed with a Kjeldahl nitrogen determination.

Reagents:

1. Boric Acid Solution, 2%
2. Potassium Sulfate
3. Concentrated Sulfuric Acid
4. Phenolphthalein Solution
   1% in 95% ethanol.
5. Hengar Granules for Nitrogen Determinations
6. Methyl Purple Indicator Enzyme Preparation Prepare an enzyme solution with the sample of known hemoglobin activity so that a 5 ml. aliquot of the final dilution will give a $\Delta N^{1.5}$ of 10–12. Refer to the calculations for help in approximating the enzyme dilution.

Kjeldahl Procedure

1. Carry assay through steps 1–6 as described in the colorimetric procedure. Run duplicate blanks and triplicate enzyme digests.

2. Into a 100 ml. Kjeldahl flask containing 4.0 gm. of potassium sulfate and 1 selenized granule, pipette 10 ml. of blank filtrate. Prepare flasks for each enzyme digest sample in the same manner using 4 ml. of filtrate.

3. Pipette 4 ml. of concentrated sulphuric acid into each flask and digest for a period of thirty minutes after clearing occurs. Turn off heat and allow flasks to cool. Add 40 ml. of distilled water and 1 drop of phenolphthalein solution. Place flasks in an ice bath for ten to thirty minutes.

4. Check the pH of the 2% boric acid solution immediately preceeding a series of distillations. Boric acid solution should be pH 4.3 to 4.7. Position the delivery tube of the distillation condenser so it dips into 40 ml. of boric acid solution contained in a 150 ml. beaker.

5. Add 7.0 grams of sodium hydroxide to the cooled Kjeldahl flask. Do not mix. Immediately attach the flasks to the distillation apparatus by means of a rubber sleeve. Mix vigourously. Distill for three minutes, lower the beaker of boric acid, and continue distillation for one minute. If bumping should occur, continue immediately as if distillation was complete. Rinse the delivery tube into the boric acid solution with distilled water. Remove the flame from under the flask.

6. Add two drops of methyl purple indicator and titrate each distillate to pH 4.5 with 0.02N hydrochloric acid. Determine the average titre for blanks and enzyme digests. Use the average titre for HU/gm calculations.

Calculations

The mg. of nitrogen in 10 ml. of filtrate due to protease hydrolysis is calculated as follows:

mg. nitrogen ($\Delta N$)=(Sample titer×10/4−Blank titer)(0.02N)(14)

mg. nitrogen ($\Delta N$)=(Sample titer×2.5−Blank titer) (0.28)

10/4=conversion of 4 ml. of sample filtrate to 10 ml. basis 0.02N=normality of hydrochloric acid 14=molecular weight of nitrogen The quantity $\Delta N$ is raised to the 1.5 power, i.e. $\Delta N^{3/2}$. If $\Delta N^{3/2}$ versus mg. enzyme is plotted, a straight line is obtained. From the straight line plot determine the weight of enzyme needed to liberate exactly 5 mg. N.

$$(\Delta N)^{1.5} = antilog\ (1.5 \times log\ \Delta N)$$

Hemoglobin Units per gram (HU/gm) are calculated as follows:

$$HU/gm = \frac{(\Delta N)^{1.5} \times 1,000 \times 60}{E \times 10} = \frac{11.18 \times 6,000}{E}$$

$(\Delta N)^{1.5}$=5 mg of nitrogen liberated in 10 ml. of filtrate 1,000=conversion of mg. enzyme to gm. enzyme 10=conversion of 10 ml. aliquot to 60 ml. total volume basis E=mg. enzyme to give 5 mg. N Calculate the F factor for the type protease as follows:

$$\underline{F} = \frac{W}{\Delta A} \times HU/gm$$

W=mg. of enzyme added to digest in 5 ml. aliquot $\Delta A$=absorbance of enzyme digest filtrate at 660 mµ

HU/gm.=hemoglobin units per gram of protease as determined by Kjeldahl standardization procedure 1 Vitapharm protease unit. (1 VPPV)=1 HU B. Amylase Units One Vitapharm amylase unit is defined as the amount of activity which liberates one milligram of reducing sugar as maltose in 30 minutes under conditions of the Vitapharm Amylase Assay, described hereunder.

Assay

Reagents

Starch Substrate 4% w/v Soluble Starch Solution

Slurry 20.00 gm. (moisture-free-basis) of soluble starch (Merck Reagent Soluble Starch suitable for Iodometry, Merck & Co., Rahway, N.J.) in 75 ml. distilled water. With agitation add the slurry to 300 ml. of vigorously boiling distilled water. Allow the starch solution to come to boiling again and gently boil for three minutes. Remove from heat and quantitatively transfer to a 500 ml. Pyrex volumetric flask. Cool to room temperature under tap water and make-up volume.

Starch Indicator Solution

Dissolve 150 gm. of analytical grade sodium chloride (NaCl) in 480 ml. distilled water and heat to boiling. Stir vigorously with a motor-driven stirrer. Slowly add a smooth suspension of 5.7 gm. (approximately 5.0 gm. dry weight) of soluble starch in 20 ml. distilled water. Boil for at least five minutes and cool.

Sodium Carbonate Solution, 10.6%

Sodium carbonate solution, 1.06%

Stock Iodine Solution, 0.1N

Dissolve 12.7 gm. iodine ($I_2$) and 48 gm. potassium iodide (KI) in approximately 900 ml. distilled water. Quantitatively transfer to a liter volumetric flask and make-up to volume with distilled water.

Iodine Solution, 0.02N

Sulfuric Acid, 0.5N

Sodium Thiosulfate, 0.005N

Enzyme Solution

The enzyme solution should be of such concentration that 1 ml. will produce approximately 20% theoretical maltose during the incubation period. Amylases are unstable in dilute solution. The appropriate enzyme solution should therefore, be prepared immediately before use. Do not equilibrate the enzyme solution at 40° C. because of the danger of inactivation.

Procedure

1. Pipette 25 ml. of 4% starch substrate into a 50 ml. volumetric flask. Add 5 ml. of the appropriate buffer and 18 ml. of water. Equilibrate the flask in a 40° C.±0.5° water bath for 15 minutes.

2. At zero time, rapidly pipette 1 ml. of the appropriate enzyme solution into the equilibrated starch mixture. Make-up to volume (with distilled water) and mix by inversion. For a substrate blank add 1 ml. distilled water instead of the enzyme solution.

3. After each reaction flask has incubated exactly 30 minutes, pipette 5 ml. of the starch digest into a 10 ml. volumetric flask containing 1 ml. of 10.6% sodium carbonate. Make-up to volume with distilled water and mix by inversion.

4. Determine the reducing value of the digest as follows: Pipette 2 ml. aliquots of the sodium carbonate enzyme digest into 50 ml. glass stoppered flasks. Duplicate all determinations. Pipette 3 ml. of 0.02N iodine solution into the glass flask and rinse the flask sides with 3 ml. of distilled water. Equilibrate the iodine mixture in a 20° C.±0.5° C. water bath for 30 minutes. Add 1 ml. of 0.5N sulphuric acid and titrate with 0.005N standardized sodium thiosulphate. Add three (3) drops of starch solution indicator as the solution becomes pale yellow. Continue titrating until the starch-iodine complex disappears.

5. For an iodine blank titrate 3 ml. of 0.02N iodine solution, 2 ml. of 1.06% sodium carbonate, and 3 ml. of water.

Calculations

Calculate the reducing values of the digest as follows:

1. Calculate the starch blanks by subtracting the starch solution titer from the iodine blank titer.

2. Calculate the mg. maltose using the following formula:

$$\text{mg. maltose} = (I_2 \text{ Blank} - \text{Starch Blank} - Na_2S_2O_3 \text{ Titre}) \times 50 \times 0.855$$

The reducing value of the sample titrated equals the iodine blank minus the starch blanks minus the sodium thiosulfate titration of the digest multiplied by 0.855. 1 ml. of 0.005N sodium thiosulfate is equivalent to 0.885 mg. maltose. The sample titrated is equivalent to 1 ml. of the original digest. The reducing value of the sample titrated multiplied by 50 gives the actual mg. of reducing sugar calculated as maltose obtained from 1 gm. of starch.

3. Correct hydrolysis values to 20% hydrolysis using the attached correction factors in Table 2. Calculate the amylase potency using the following equation:

$$\text{mg/mg potency} = \frac{\text{mg maltose} \times \text{correction factor}}{\text{mg/ml enzyme}}$$

TABLE 2

Correction Factors Bacterial Amylase

| Calc. mg. Maltose | Correction Factors to Convert to 20% | Calc. mg. Maltose | Correction Factors to Convert to 20% | Calc. mg. Maltose | Correction Factors to Convert to 20% |
|---|---|---|---|---|---|
| 86 | .82 | 175 | .94 | 265 | 1.14 |
| 90 | .83 | 180 | .95 | 270 | 1.16 |
| 94 | .83 | 184 | .95 | 274 | 1.18 |
| 98 | .84 | 188 | .95 | 278 | 1.20 |
| 103 | .84 | 192 | .97 | 282 | 1.24 |
| 107 | .85 | 197 | .98 | 287 | 1.28 |
| 111 | .86 | 201 | .98 | 291 | 1.31 |
| 115 | .86 | 205 | .99 | 295 | 1.35 |
| 120 | .87 | 210 | 1.00 | 299 | 1.39 |
| 124 | .87 | 214 | 1.00 | 304 | 1.44 |
| 128 | .88 | 218 | 1.01 | 308 | 1.48 |
| 133 | .89 | 223 | 1.03 | 312 | 1.53 |
| 137 | .89 | 227 | 1.04 | 316 | 1.57 |
| 141 | .90 | 231 | 1.05 | 321 | 1.63 |
| 145 | .90 | 235 | 1.06 | 325 | 1.69 |
| 150 | .91 | 240 | 1.07 | 329 | 1.75 |
| 154 | .91 | 244 | 1.08 | 333 | 1.81 |
| 158 | .92 | 248 | 1.09 | 338 | 1.90 |
| 162 | .92 | 252 | 1.10 | 342 | 1.97 |
| 167 | .93 | 257 | 1.11 | 347 | 2.05 |
| 171 | .94 | 261 | 1.13 | 351 | 2.13 |

C. Lipase Units

One Vitapharm lipase unit is defined as that activity which will liberate one milli equivalent of fatty acid in two hours using a Vitapharm Amylase Assay described hereunder.

Assay

Reagents

1. Buffer, 0.1M Phosphate, pH 7.3

Dissolve 2.780 gm. of $NaH_2PO_4 \cdot H_2O$ in water and dilute to 100 ml. Dissolve 2.839 gm. of anhydrous $Na_2HPO_4$ in water and dilute to 100 ml. Measure 23.0 ml. of the $NaH_2PO_4$ solution and 77.0 ml. of the $Na_2HPO_4$ solution into a 200 ml. volumetric flask and bring to volume with distilled water.

2. Substrate, Olive Oil Emulsion

Slowly add 200 mg. of sodium benzoate and 7.0 grams of USP Gum Arabic to 93 ml. of 0.1M phosphate buffer in a Waring Blender running at slow speed (by using a Powerstat set at 25 to 30). When these reagents are completely dissolved, slowly add 93 ml. of USP Olive Oil. When all the oil has been added, blend at this speed for 3 minutes and &hen at high speed for 5 minutes.

3. Buffered Substrate

Into a tared 100 ml. volumetric flask add 54.40 gm. of the olive oil emulsion and bring to volume with the 0.1M phosphate buffer solution. This buffered substrate should have a pH of 7.3.

4. Ethyl Alcohol, 95%

5. Thymolphthalein, 1% (w/v) in 95% ethyl alcohol

6. Sodium Hydroxide, 0.05N

Procedure

1. Pipette 5.0 ml. aliquots of the buffered substrate into 50 ml. Erlenmeyer flasks. One flask is required for each sample to be assayed. Place these in a special holding clamp and set in a 37° C. water bath.

2. Prepare a suitable dilution of the enzyme. Sample dilution will depend on the lipase activity of the preparation.

3. Add 5.0 ml. of distilled water to one flask containing the substrate. This constitutes an enzyme blank. Then add 5.0 ml. of each enzyme sample to other substrate flasks. Mix well and incubate for exactly 2 hours at 37° C. Swirl the flasks occasionally.

4. Stop reaction by adding 3.0 ml. of ethyl alcohol to the flasks, add 4 drops of thymolphthalein and mix thoroughly.

5. Titrate each flask with 0.05N NaOH to a pale blue end point. It is preferable to titrate the blank and then match the samples to it. For measure of enzyme action, subtract blank titration from sample titration.

Calculation

The extent of hydrolysis of the substrate by different levels of enzyme is not linear. In order to obtain good reproducibility, the amount of enzyme required to give a titration difference (sample titer-blank titer) of 4.0 ml. of 0.05N NaOH is the correct amount of enzyme. There are two procedures that can be used to determine this amount of enzyme.

A. Three Sample Method

Three samples of the enzyme preparation are run exactly according to the procedure, the weights of samples being chosen so that one will give a titration difference somewhat less than 4.0 ml., another somewhat above 4.0 ml., and the third approximately equal to 4 ml. On coordinate graph paper, plot the mg. of enzyme against titration difference and draw a straight line between the points. From the plot read the mg. enzyme for exactly 4.0 ml. titration difference and use this value to calculate lipase units from the formula:

$$\frac{4.0 \times N \times 1000}{\text{mg. enzyme sample}} = \text{Lipase units } (LU)/gm. \text{ where } N \text{ equals the normality of NaOH.}$$

B. Standard Curve Method

Employing as a standard sample a preparation the activity of which has been accurately determined, run assays exactly according to the procedure employing several different sample weights of the standard sample. Plot the titration differences obtained against mg. of standard sample, and draw a smooth curve through the points. Having established this standard curve, to determine the lipase activity of an unknown sample, run an assay with a convenient sample weight according to the procedure. From the standard curve determine the weight of standard sample which gives the same titration difference as the unknown assay sample and calculate lipase units by the relation:

$$LU/gm = \frac{\text{mg. standard sample}}{\text{mg. unknown sample}} \times \text{assay of standard sample}$$

D. Cellulase Units

One Vitapharm cellulase unit is defined as that activity which will produce a relative fluidity change of one in five minutes in a defined carboxymethyl cellulose substrate under assay conditions. The assay is based on enzymatic hydrolysis of the interior beta-1,4-glucosidic bonds of a defined carboxymethyl cellulose substrate at pH 4.5 and 40° C.

Reagents and Solutions

1. Acetic Acid Solution, 2N
2. Sodium Acetate Solution, 2N
3. Acetic Acid Solution, 0.4N
4. Sodium Acetate Solution, 0.4N
5. Acetate Buffer (pH 4.5)

Using a standardized pH meter, add sodium acetate solution (0.4N) with continuous agitation to 400 ml. of acetic acid solution (0.4N) until the pH is 4.5±0.05.

6. Sodium Carboxymethyl Cellulose

Use sodium carboxymethyl cellulose designated CMC Type 7HP, Hercules, Inc., 910 Market Street, Wilmington, Del. 19899.

7. Sodium Carboxymethyl Cellulose Substrate, 0.2% w/v

Transfer 200 ml. of distilled water into the bowl of the Waring Blender. With the blender on low speed, slowly disperse 1.0 g. (moisture-free basis) of CMC 7HP into the bowl being careful not to splash out any of the liquid. Wash down the sides of the glass bowl with distilled water using a rubber policeman. Place the top on the bowl and blend at high speed for 1 minute. Quantitatively transfer to a 500 ml. volumetric flask and dilute to volume with distilled water. Filter the substrate through gauze prior to use.

Enzyme Preparation

Prepare an enzyme solution so that 1 ml. of the final dilution will produce a relative fluidity change between 0.18 and 0.22 in 5 minutes under the conditions of the assay. Weigh the enzyme and quantitatively transfer to a glass mortar. Triturate with distilled water and quantitatively transfer to an appropriate volumetric flask. Dilute to volume with distilled water and filter the enzyme solution through Whatman No. 1 filter paper prior to use.

Assay Procedure

1. Place the calibrated viscometer in the 40°±0.1° C. water bath in an exactly vertical position. Use only a scrupulously clean viscometer. Cleaning is readily accomplished by drawing a large volume of detergent solution followed by distilled water through the viscometer. This can be accomplished using an aspirator with a rubber tube connected to the narrow arm of the viscometer.

2. Pipette 20 ml. of filtered CMC 7HP substrate and 4 ml. of acetate buffer (pH 4.5) into a 50 ml. Erlenmeyer flask. Allow at least two flasks for each enzyme sample and one flask for a substrate blank. Stopper the flasks and equilibrate them in the water bath for 15 minutes.

3. At zero time pipette 1 ml. of the enzyme solution into the equilibrated substrate. Start stopwatch No. 1 and mix solution thoroughly. Immediately pipette 10 ml. of the reaction mixture into the wide arm of the viscometer.

4. After approximately 2 minutes apply suction with a rubber tube connected to the narrow arm of the viscometer, drawing the reaction mixture above the upper mark into the drive fluid head. Measure the efflux time by allowing the reaction mixture to freely flow down past the upper mark. As the meniscus of the reaction mixture falls past the upper mark start stopwatch No. 2. At the same time record the reaction time in minutes from stopwatch No. 1 ($T_r$). As the meniscus of the reaction mixture falls past the lower mark, record the time in seconds from stopwatch No. 2 ($T_t$).

5. Immediately re-draw the reaction mixture above the upper mark, into the driving fluid head. As the meniscus of the reaction mixture falls freely past the upper mark, re-start stopwatch No. 2. At the same time record the reaction time in minutes from stopwatch No. 1 ($T_r$). As the meniscus of the reaction mixture falls past the lower mark, record the time in seconds from stopwatch No. 2 ($T_t$).

6. Repeat step five until a total of four determinations is obtained over a reaction time ($T_r$) of not more than 15 minutes.

7. Prepare a substrate blank by pipetting 1 ml. of distilled water into 24 ml. of buffered substrate. Pipette 10 ml. of the reaction mixture into the wide arm of the viscometer. Determine the time ($T_s$) in seconds required for the meniscus to fall between the two barks. Use an average of 5 determinations for ($T_s$).

8. Prepare a water blank by pipetting 10 ml. of equilibrated distilled water into the wide arm of the viscometer. Determine the time ($T_w$) in seconds required for the meniscus to fall between the two marks. Use an average of 5 determinations for ($T_w$).

Calculations

One Cellulase Unit (CU) is that activity which will produce a relative fluidity change of 1 in 5 minutes in a defined carboxymethyl cellulose substrate under the conditions of assay.

Calculate the relative fluidities ($F_r$) and the ($T_M$) values for each of the four efflux times ($T_t$) and reaction times ($T_r$) as follows:

$F_r = (T_s - T_w)(T_t - T_w)$ $T_m = \frac{1}{2}(T_t/60 \text{ sec./min.}) + T_r = (T_2/120) + T_r$ Where:

$F_r$ = relative fluidity for each reaction time
$T_s$ = average efflux time for the substrate blank in seconds
$T_w$ = average efflux time for the water blank in seconds
$T_t$ = efflux time of reaction mixture in seconds $T_r$=elapsed time in minutes from zero time; i.e. the time for addition of the enzyme solution to the buffered substrate until the beginning of the measurement of efflux time ($T_r$)

$T_M$=reaction time in minutes ($T_r$), plus one-half of the efflux time ($T_e$) converted to minutes.

Plot the four relative fluidities ($F_r$) as the ordinate against the four reaction times ($T_N$) as the abscissa. A straight line should be obtained. The slope of this line corresponds to the relative fluidity change per minute and is proportional to the enzyme concentration. The slope of the best line through a series of experimental points is a better criterion of enzyme activity than is a single relative fluidity value. From the graph determine the $F_r$ values at 10 and 5 minutes. They should have a difference in fluidity of not more than 0.22 nor less than 0.18. Calculate the activity of the enzyme unknown as follows:

$$CU/g = \frac{1000F(F_{r10} - F_{r5})}{W}$$

Where:
$F_{r5}$=relative fluidity at 5 minutes of reaction time
$F_{r10}$=relative fluidity at 10 minutes of reaction time
1000=milligrams per gram
W=weight in milligrams of enzyme added to the reaction mixture in a 1 ml. aliquot of enzyme solution.

I claim:

1. An animal growth promotant comprising microgranules having a core consisting of at least one digestive enzyme immobilized by entrapment within a gel matrix wherein said gel matrix restricts the accessibility of denaturing agents to said at least one digestive enzyme, wherein said at least one digestive enzyme is selected from the group consisting of:
    (i) protein digesting enzymes;
    (ii) carbohydrate digesting enzymes;
    (iii) fat digesting enzymes; and
    (iv) fibre digesting enzymes;
wherein the core is encapsulated within a water soluble film, and coated with an enteric coating comprising an alkali soluble, acid insoluble polymer, or a high molecular weight polymer whose structure is substituted with or contains windows of fatty acid or other material capable of being solubilized by intestinal juices, whereby said at least one digestive enzyme is not degraded by contact with fluids in the stomach or rumen.

2. An animal growth promotant as claimed in claim 1, wherein the gel matrix comprises k-carrageenan; gelatin; aliginates; cellulose or its derivatives; or gel forming synthetic polymers.

3. An animal growth promotant as claimed in claim 1 wherein the microgranules have a size between 25 and 500 μm.

4. An animal growth promotant as claimed in claim 3, wherein the microgranules have a size between 50 and 350 μm.

5. An animal growth promotant as claimed in claim 1, wherein the windows of fatty acid or other material in the high molecular weight polymer comprise $C_{12}$–$C_{24}$ fatty acids.

6. An animal growth promotant as claimed in claim 1, wherein the water soluble film is a gelatin film.

7. An animal growth promotant as claimed in claim 1, wherein the alkali soluble, acid insoluble polymer is cellulose acetate phthalate.

8. An animal growth promotant as claimed in claim 1, wherein the high molecular weight polymer is butyl methylacrylate.

9. An animal growth promotant as claimed in claim 1 containing:
    $2 \times 10^3$ to $2 \times 10^7$ protease units
    $1 \times 10^4$ to $4.3 \times 10^8$ amylase units
    0.5 to $5 \times 10^3$ lipase units
    $2 \times 10^2$ to $2 \times 10^6$ cellulase units,
per kilogram of said animal growth promotant.

10. Animal feed in admixture with an animal growth promotant as claimed in claim 1.

11. An animal growth promotant composition comprising an animal growth promotant as claimed in claim 1 in association with a pharmaceutically or veterinarily acceptable carrier or excipient.

12. Animal feed in admixture with an animal growth promoting composition as claimed in claim 11.

13. A method for the production of an animal growth promotant comprising the steps of:
    (a) immobilizing at least one enzyme selected from the group consisting of
        (i) protein digesting enzymes;
        (ii) fat digesting enzymes;
        (iii) fibre digesting enzymes;
        (iv) carbohydrate digesting enzymes; by entrapment within a core;
    (b) microgranulating the immobilized at least one enzyme;
    (c) encapsulating the microgranules with a water soluble mechanical barrier; and
    (d) coating the microgranules of step (c) with an enteric coating comprising an alkaline soluble, acid insoluble polymer, or a high molecular weight polymer whose structure is substituted with or contains windows of fatty acid or other material capable of being solubilized by intestinal juices.

14. A method as claimed in claim 13 herein at least one enzyme is immobilized within a gel material.

15. A method as claimed in claim 13, wherein the microgranules are spray coated with the water soluble mechanical barrier of step (c) and the coating of step (d).

16. A method for administering an animal growth promotant to animals in need thereof, comprising administering to said animal growth promotant comprising microgranules having a core consisting of at least one digestive enzyme immobilized by entrapment within a gel matrix wherein said gel matrix restricts the accessibility of denaturing agents to said at least one digestive enzyme, said at least one digestive enzyme being selected from the group consisting of:
    (a) protein digesting enzymes;
    (b) carbohydrate digesting enzymes;
    (c) fat digesting enzymes;
    (d) fibre digesting enzymes;
the core being encapsulated within a water soluble film, and coated with an enteric coating comprising an alkali soluble, acid insoluble polymer, or a high molecular weight polymer whose structure is substituted with or contains windows of fatty acid or other material capable of being solubilized by intestinal juices, whereby said at least one digestive enzyme is not degraded by contact with fluids in the stomach or rumen.

17. The method according to claim 16 wherein the gel matrix of said animal growth promotant comprises k-carrageenan; gelatin; alginates; cellulose or its derivatives; or gel forming synthetic polymers.

18. The method according to claim 16 wherein said microgranules in said animal growth promotant have a size between 25 and 500 μm.

19. The method according to claim 18 wherein said microgranules have a size between 50 and 350 μm.

20. The method according to claim 16 wherein the windows of fatty acid or other material in the high molecular weight polymer in said animal growth promotant comprise $C_{12}$–$C_{24}$ fatty acids.

21. The method according to claim 16 wherein the water soluble film in said animal growth promotant is a gelatin film.

22. The method according to claim 16 wherein the alkali soluble, acid insoluble polymer in said animal growth promotant is cellulose acetate phthalate.

23. The method according to claim 16 wherein the high molecular weight polymer in said animal growth promotant is butyl methacrylate.

24. The method according to claim 16 wherein the animal growth promotant contains:

$2\times10^3$ to $2\times10^7$ protease units $1\times10^4$ to $4.3\times10^8$ amylase units 0.5 to $5\times10^3$ lipase units $2\times10^2$ to $2\times10^6$ cellulase units per kilogram of said animal growth promotant.

25. The method according to claim 16 wherein said animal growth promotant is in association with a pharmaceutically or veterinarily acceptable carrier or excipient.

26. The method according to claim 16 wherein said animal growth promotant is administered in animal feed.

* * * * *